United States Patent [19]

Rahm et al.

[11] 4,316,872
[45] Feb. 23, 1982

[54] RING OF CELLS FOR ANALYTICAL DEVICES

[75] Inventors: Juerg Rahm, Basel, Switzerland; Peter Schulz, Pfreimd, Fed. Rep. of Germany

[73] Assignee: Hoffmann-La Roche Inc., Nutley, N.J.

[21] Appl. No.: 146,987

[22] Filed: May 5, 1980

[30] Foreign Application Priority Data

May 10, 1979 [DE] Fed. Rep. of Germany ....... 2913501
May 10, 1979 [DE] Fed. Rep. of Germany ....... 2918800

[51] Int. Cl.³ .............................................. G01N 35/00
[52] U.S. Cl. ....................................... 422/102; 422/72; 206/219; 220/23.4; 356/246
[58] Field of Search ............... 422/72, 102; 233/26, 233/21, 16; 206/219; 220/23.4; 356/246

[56] References Cited

U.S. PATENT DOCUMENTS 3,521,785  7/1970  Bergmann et al. ............. 220/23.4
4,123,173  10/1978  Bullock ........................... 356/246

FOREIGN PATENT DOCUMENTS 2726219  12/1977  Fed. Rep. of Germany .

OTHER PUBLICATIONS

COBAS BIO, Roche Brochure 1978.
COBAS BIO, Roche Brochure 1979.

Primary Examiner—William F. Smith
Attorney, Agent, or Firm—Jon S. Saxe; Bernard S. Leon; George W. Johnston

[57] ABSTRACT

A ring of cells for analytical devices operating on the centrifugal principle and photometrically measuring a sample for analysis, the system comprising a number of individual cells disposed in a circle and made of thermoplastics, each cell having three interconnected chambers, i.e. a sample chamber, a reagent chamber and a photometric measuring chamber, the major axes of the sample chamber and the reagent chamber being at right angles to the plane of rotation and the major axis of the measuring chamber coinciding with the plane of rotation. In order to simplify and thus reduce the cost of the ring of cells, each cell at its upper edge has a laterally projecting tongue which completely or partly overlaps the adjacent cell and is secured thereto. It is particularly advantageous to use the above ring of cells in a centrifugal analyzer for clinical chemistry.

15 Claims, 2 Drawing Figures

RING OF CELLS FOR ANALYTICAL DEVICES

BACKGROUND OF THE INVENTION

The invention relates to a ring of cells for analytical devices operating on the centrifugal principle and photometrically measuring a sample for analysis, the system comprising a number of individual cells disposed in a circle and made of thermoplastics, each cell having three interconnected chambers, i.e. a sample chamber, a reagent chamber and a photometric measuring chamber, the major axes of the sample chamber and the reagent chamber being at right angles to the plane of rotation and the major axis of the measuring chamber coinciding with the plane of rotation.

Some known analytical devices operate on the centrifugal principle and make photometric measurements of the sample for analysis. They are preferably used when very small samples have to be analysed in a short time and where the nature of the analysis is such that photometric methods can be used. This applies particularly to clinical chemical analysis, where it is frequently necessary e.g. to determine glucose, urea, uric acid, cholesterol or total protein, albumin, bilirubin or metal ions in the blood, serum, plasma, urine or liquid obtained by puncture, e.g. liquor or similar biological solutions. The amount of material available for investigation is frequently only a few microliters and the time available for analysis is often limited to a few minutes. In such cases it is advantageous to use automatic analytical devices operating by the aforementioned centrifugal method.

The devices comprise a ring of cells containing a predetermined number of individual cells. Each individual cell has at least three chambers, i.e. a sample chamber, a reagent chamber and a photometric measuring chamber. The sample and the reagent are poured into the appropriate cell chambers when the rotor is motionless, so that the two liquids initially remain separate. After the cells have been filled, the analyzer is started up, whereupon the centrifuge first rotates at high speed. As a result of centrifugal force, the sample for analysis and the reagent liquid are expelled from the two chambers into which they were previously poured, and are combined and raised to the photometric measuring chamber. After a predetermined time, the photometric scanning of the individual measuring chamber begins, and usually the peripheral speed of the centrifugal part of the analyzer is reduced. The extinction recorded by the measuring part is evaluated by a computer and is usually immediately expressed as the result of the analysis.

Known centrifugal analyzers of this kind, e.g. as described in the "Cobas-Bio" pamphlet published in 1978 by Messrs. F. Hoffmann-Laroche & Co. of Basle, comprise a number of individual cells combined to form the aforementioned ring of cells by means of a separate ring. The ring has a number of radial slots in which the cells with their oblong measuring chambers are inserted and retained. The advantage of the device is that individual cells can be thrown away after use and destroyed if necessary, which is particularly important in the analysis of pathogenic liquids.

German Offenlegungsschrift No. 27 26 219 corresponding to U.S. Pat. No. 4,123,173 discloses a cell system for centrifugal analyzers having a different construction. According to the last citation, the cell system comprises two superposed discs of flexible thermoplastics, the lower disc being formed with a number of compartments and the top disc being stuck or welded to the bottom disc and, in the process, covering at least part of each compartment. Cell systems of this kind form an inseparable unit which, as before, has good mechanical stability but where it is impossible to remove individual cells from the unit and destroy them separately.

SUMMARY OF THE INVENTION

An object of the invention is to simplify and thus reduce the cost of annular cell systems of the kind described in the "Cobas-Bio" pamphlet. The object of the simplification is to do without the retaining ring without giving up the advantage of separating individual cells.

To this end, according to the invention, each cell at its upper edge has a laterally projecting tongue which completely or partly overlaps the adjacent cell and is secured thereto. According to a particularly advantageous feature, the tongue is secured, preferably by welding, to the top edge of the next-but-one side wall of the next cell. As a result of this feature, the ring of cells has sufficient dimensional stability and strength to withstand normal handling and the stress during centrifuging. It has been found that the required strength can also be obtained if the tongue covers only the rear part of the neighbouring cell in the radial direction but leaves the front part uncovered. This is advantageous in that it facilitates the process of filling individual cells when the ring is at a standstill.

According to another proposed feature of the invention, each cell has a web above the connecting aperture between the sample chamber and reagent chamber on the one hand and the measuring chamber on the other hand.

The web can be constructed with thick portions at its ends and so that the lateral end surfaces of the web of neighbouring cells abut and are interconnected if required. The webs prevent the sample or reagent liquid from accidentally reaching the relatively sensitive components of the centrifugal analyzer. The webs also support one another and further increase the strength of the ring of cells. The webs also combine to form a convenient handle for holding the device. In spite of the resulting considerable radial strength, which easily withstands stresses during centrifuging, it is possible to break individual cells from the ring and use them as partial segments in the analyzer when only a few samples needs to be analyzed.

BRIEF DESCRIPTION OF THE DRAWINGS

Some embodiments of the invention will now be described with reference to the accompanying drawings, in which.

DESCRIPTION OF THE PREFERRED EMBODIMENTS

Figure 1:
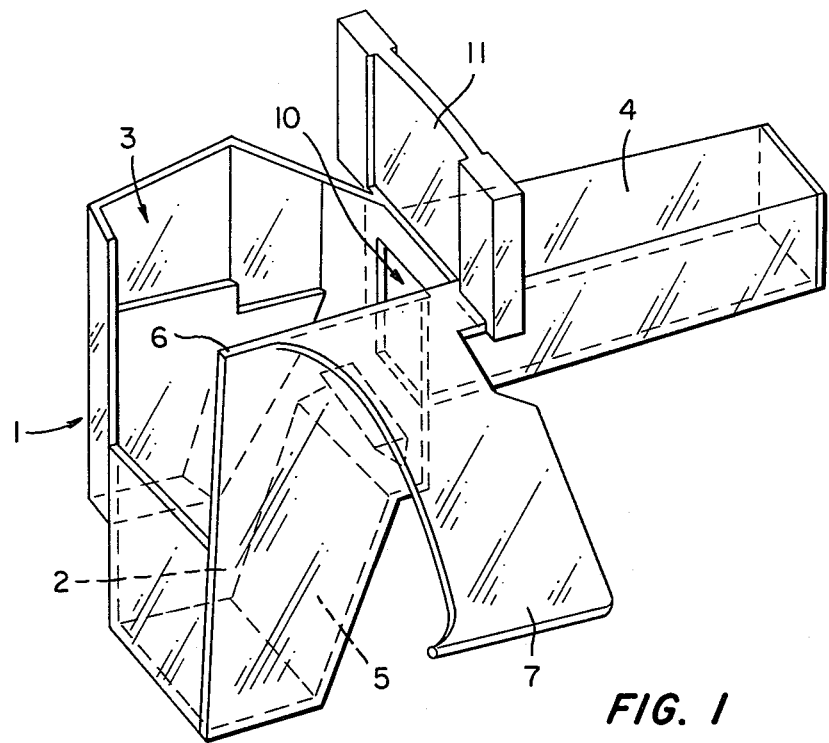
FIG. 1 is a perspective view of an embodiment of a single cell in a ring of cells according to the invention.

FIG. 1 shows an individual cell (general reference 1). The cell is made up of a total of three chambers, i.e. a reagent chamber 2, a sample chamber 3 and a photometric chamber 4. The major axes of the reagent chamber and the sample chamber are at right angles to the plane of rotation of the analyzer whereas the major axis of the measuring chamber 4 is in the plane of rotation. FIG. 1 also shows that the back wall of the reagent chamber, in centrifugal direction, is oblique. The corresponding wall of the sample chamber (not shown in the drawing) is likewise oblique. If the ring of cells, i.e. each individual cell, is centrifuged, the liquid in the reagent chamber and the sample chamber rises along the oblique wall and the liquids mix and enter the measuring chamber 4.

Figure 2:
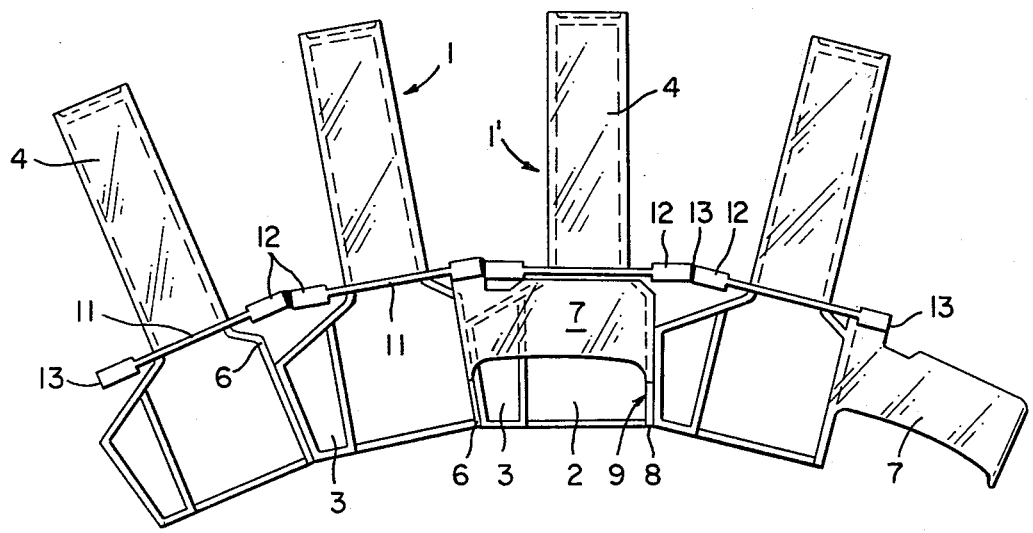
FIG. 2 is a plan view of a portion of a ring of cells according to the invention.

According to the invention, the upper edge 6 of each cell 1 has a laterally projecting tongue 7 which partly or completely covers and is secured to the neighbouring cell in the ring. FIG. 2 shows a preferred embodiment in which tongue 7 is secured to the top edge 8 of the next-but-one side wall 9 of the next cell 1', preferably by welding. One result of this overlap is that the reagent and cell chambers, which are open at the top, are covered by the overlapping tongue. Another result is that the entire ring of cells has higher stability, since the top edges of the chamber walls abut the under-surface of the tongue.

The drawing also shows that in the embodiment depicted therein tongue 7 covers only the rear part, in the centrifugal direction, of the corresponding adjacent cell.

According to another proposed feature of the invention, each cell 1 has a web 11 above the connecting aperture 10 between the sample chamber and reagent chamber on the one hand and the measuring chamber on the other hand. The web preferably has thick ends 12, which increases the stability and also enables the lateral end-faces 13 of the webs to abut and be interconnected if required, likewise by welding or sticking. The webs thus form a handle which simplifies manipulation of the ring of cells.

Preferably the ring of cells is made of transparent, unstabilized polymethyl methacrylate (PMMA).

We claim:

1. A cell for a ring of cells of an analytical device operating on the centrifugal principle utilizing a reagent for measuring a sample, said cell comprising:
   (a) a sample chamber configured and disposed to receive and retain the sample until centrifugal force is applied to the cell;
   (b) a reagent chamber configured and disposed to receive and retain the reagent until centrifugal force is applied to the cell;
   (c) a measuring chamber having an opening communicating the sample chamber and reagent chamber therewith, said measuring chamber configured and disposed to receive and retain the sample and reagent while centrifugal force is applied to the cell;
   (d) tongue means integral with the cell, positioned and configured to project from the cell and at least partially overlap a portion of an adjacent cell, said tongue means being secured to said adjacent cell so as to form a rigid connection between said adjacent cells; and
   (e) an integral web member positioned above the measuring chamber and configured and dimensioned so as to retain the reagent and sample within the cell while centrifugal force is applied to the cell.

2. A ring of cells for an analytical device operating on the centrifugal principle for photometrically measuring a sample, said ring comprising individual cells disposed in a circle, each cell having a sample chamber, a reagent chamber and a photometric measuring chamber communicating with each other by an aperture in the measuring chamber, the major axis of the sample chamber and the reagent chamber approximately being at right angles to the plane of rotation of the ring and the major axis of the measuring chamber approximately coinciding with the plane of rotation, each cell having at its upper edge a laterally projecting tongue which at least partly overlaps an adjacent cell and is secured thereto so as to form a rigid ring of cells, and each cell having a web integral therewith and positioned above the aperture of the measuring chamber.

3. The ring of cells of claim 2 wherein the web is configured and dimensioned to project upwardly from the plane of rotation of the ring and thereby reduce spillage of the sample from the cell during rotation.

4. The ring of cells of claim 2 or 3 wherein the web has a central portion and end portions, said end portions being contiguous with adjacent cells and thicker than the central portion.

5. The ring of cells of claim 4 wherein the end portions of the web have lateral end surfaces which abut the web of an adjacent cell.

6. The ring of cells of claim 2 wherein the tongue is secured to the adjacent cell by welding or gluing so as to form a rigid ring of cells.

7. The ring of cells of claim 2 wherein at least one cell is made of a thermoplastic.

8. A ring of cells for an analytical device operating on the centrifugal principle for photometrically measuring a sample while the ring is rotating, said ring comprising a multiplicity of cells disposed adjacently in a circle, each cell having a sample chamber, a reagent chamber and a photometric measuring chamber connected to each other by an aperture in the measuring chamber, the major axis of the sample chamber and the reagent chamber being approximately at right angles to the plane of rotation of the ring and the major axis of the measuring chamber approximately coinciding with the plane of rotation, each cell having an upper end portion with a tongue means projecting therefrom approximately parallel to the plane of rotation which at least partially overlaps an adjacent cell and is secured thereto so as to form a rigid ring of cells, each cell having an integral web means located over the photometric measuring chamber, said web means projecting upwardly approximately perpendicular to the plane of rotation of the ring and dimensioned so as to retain the sample within the cell during rotation.

9. The ring of cells of claim 8 wherein the tongue means is secured by welding or gluing to at least the adjacent cell.

10. The ring of cells of claim 8 wherein the tongue means is configured to cover the back part, in centrifugal direction, of an adjacent cell.

11. The ring of cells of claim 8 wherein the web means increases in thickness at the area contiguous with the adjacent cells.

12. The ring of cells of claim 8 wherein the web means of each cell has lateral end surfaces which abut adjacent cells.

13. The ring of cells of claim 12 wherein the web means of each cell is interconnected with each other.

14. The ring of cells of claim 8 wherein at least one cell is made of a thermoplastic.

15. The ring of cells of claim 8 wherein the web means is configured to form a handle.

* * * * *